United States Patent

Munson, Jr. et al.

[11] Patent Number: 4,803,200
[45] Date of Patent: Feb. 7, 1989

[54] SUBSTITUTED DIALKANOLAMINES, SULFUR ANALOGS AND CONDENSED 1,4-OXAZINE DERIVATIVES THEREOF IN VIRAL DISEASE TREATMENT

[75] Inventors: Harry R. Munson, Jr.; Robert W. Tankersley, Jr., both of Richmond, Va.

[73] Assignee: A. H. Robins Company, Incorporated, Richmond, Va.

[21] Appl. No.: 103,938

[22] Filed: Oct. 2, 1987

[51] Int. Cl.$^4$ ............................................ C07C 121/78
[52] U.S. Cl. .................... 514/231.2; 514/471; 514/654
[58] Field of Search ............... 514/231.2, 471, 654

[56] References Cited

U.S. PATENT DOCUMENTS 3,983,228  9/1976  Woodhour et al. ............... 514/785
4,069,313  1/1978  Woodhour et al. ............... 514/784

Primary Examiner—Curtis R. Davis

[57] ABSTRACT

Substituted dialkanolamines, oxazine and sulfur analogs thereof, useful in treating shipping fever syndrome in mammals are disclosed having the formula:

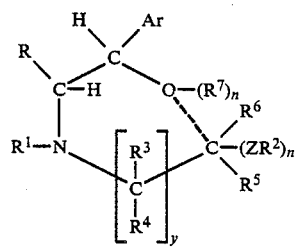

wherein:

Ar is

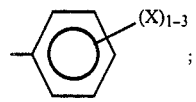

Z is oxygen or sulfur;
R is selected from hydrogen, loweralkyl or

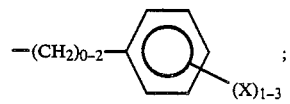

$R^1R^2$, $R^3$, $R^4$, $R^5$, $R^6$ and $R^7$ are selected from hydrogen or loweralkyl; and

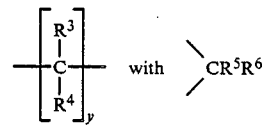

when taken together may form a lowercycloalkyl ring or $R^5$ with $-ZR^2$ when taken together may form a 5-membered saturated oxygen or sulfur containing heterocyclic ring;

X is selected from hydrogen, halo, loweralkoxy, loweralkyl, trifluoromethyl or dimethylamino and when X is more than 1, it may be the same radical or different;

y is 0, 1 or 2;

n is one, or zero and when n is 1, the stereoisomers thereof and when n is zero the dotted line becomes an oxygen-carbon bond forming an oxazine ring and the pharmaceutically acceptable acid addition salts thereof.

36 Claims, No Drawings

SUBSTITUTED DIALKANOLAMINES, SULFUR ANALOGS AND CONDENSED 1,4-OXAZINE DERIVATIVES THEREOF IN VIRAL DISEASE TREATMENT

BACKGROUND OF THE INVENTION

1. Field of Invention

This invention relates to a novel method of combating viral infections in animals, especially mammals such as cattle, sheep, goats, horses, buffalo, deer, and the like, particularly those viral infections associated with shipping fever, by administration of certain substituted dialkanolamines, thiol analogs and 1,4-oxazine condensation derivatives thereof.

Several causal factors are generally recognized as being associated with animal "shipping-fever-syndrome," mainly a combination of stress, viral infection and bacterial infection. Bovine Parainfluenza-3 (Shipping Fever-4) virus infects the respiratory tract in young animals such as calves and lambs, lowering the animals' native immunity and allowing Pasteurella bacteria and other pathogenic microorganisms to produce serious respiratory infections. The viral attack may thus be considered to have initiated the bacterial infection. In young steers, for example, shipped to a feed-lot, shipping fever may result in serious economic loss. The subject compounds administered to animals have particular utility in countering the effects of the virus and thus lessen the likelihood of bacterial infection. Stated another way, the present invention deals principally with negating the viral influence of the shipping fever syndrome and in so doing may also favorably alter animal resistance to bacterial attack.

2. Information Disclosure Statement and Prior Uses

U.S. Pat. No. 4,271,174 discloses the use of cycloserine as an antibacterial in control of the bacterial aspect of shipping fever involving Pasteurella species.

Certain of the subject compounds of the present invention were prepared and reported to be antitumor agents in the following disclosures:

R. E. Lutz and R. S. Murphey in J. Am. Chem. Soc. 71, 478 (1949),

R. E. Lutz and J. W. Baker in J. Org. Chem. 21, 49 (1956), and,

R. E. Lutz, J. A. Freek and R. S. Murphey in J. Am. Chem. Soc. 70, 2015 (1948).

Use of the compounds as antiviral agents has not previously been reported.

SUMMARY OF THE INVENTION

The substituted dialkanolamines, sulfur analogs and oxazine derivatives useful in the antiviral method of this invention have the formula:

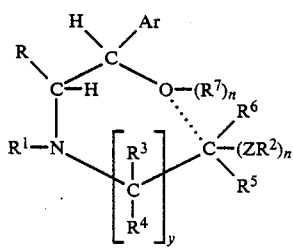

wherein;
Ar is

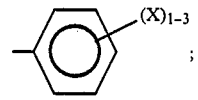

Z is oxygen or sulfur;
R is selected from hydrogen, loweralkyl or

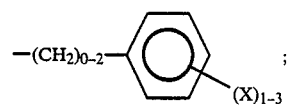

$R^1$, $R^2$, $R^3$, $R^4$, $R^5$, $R^6$ and $R^7$ are selected from hydrogen or loweralkyl; and

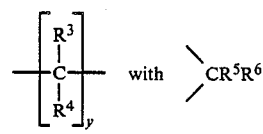

when taken together may form a lowercycloalkyl ring (3–9 carbons); or $R^5$ with $-ZR^2$ when taken together may form a 5-membered saturated oxygen or sulfur containing heterocyclic ring;

X is selected from hydrogen, halo, loweralkoxy, loweralkyl, trifluoromethyl or dimethylamino, and when X is more than 1, it may be the same radical or different;

y is 0, 1 or 2;

n is 1 or zero and when n is 1, the stereoisomers thereof, and when n is zero the dotted line becomes an oxygen-carbon bond forming a ring, and the pharmaceutically acceptable acid additions salts of all thereof.

In the further definition of symbols in the formulas hereof and where they appear elsewhere throughout this specification and claims, the terms have the following significance.

The term "loweralkyl" includes straight and branched chain hydrocarbon radicals of up to eight carbon atoms inclusive and is exemplified by such groups as methyl, ethyl, propyl, isopropyl, butyl, isobutyl, tertiary butyl, amyl, isoamyl, hexyl, heptyl, octyl, and the like.

The term "loweralkoxy" has the formula —O—loweralkyl.

The terms "halo" and "halogen" include chlorine, bromine, fluorine and iodine, preferably chlorine, bromine, and fluorine.

The term "lowercycloalkyl ring" includes cyclic radicals up to 9 carbon atoms and includes groups such as cyclopropyl, cyclobutyl, cyclopentyl, cyclohexyl, cycloheptyl, cyclooctyl and cyclononyl.

By 5-membered saturated oxygen or sulfur containing heterocyclic ring is meant tetrahydrofuran-2 or 3-yl or tetrahydrothienyl-2 or 3-yl.

The term "Ar" refers to phenyl or phenyl substituted by $(X)_{1-3}$, wherein X is as defined under Formula I.

By the use of the term "stereoisomers" is meant those stereoisomers which are possible in compounds of Formula I, wherein n is one, which meet the criteria for stereoisomerism at the sites of the carbon bearing the Ar and hydroxy (or ether) groups taken together with the adjacent carbon and its substituents. Both the erythro and threo stereoisomers are useful in the pharmaceutical method of this invention.

Pharmaceutically acceptable acid addition salts are those salts which are physiologically compatible in warm-blooded animals. The acid addition salts may be formed either by strong or weak acids. Representative of useful strong acids in salt formation are hydrochloric, hydrobromic, sulfuric, and phosphoric acids. Representative of useful weak acids in salt formation are fumaric, maleic, succinic, oxalic, citric, tartaric, hexamic and the like.

Efficacy of the compounds of Formula I was demonstrated by contacting virus infected continuous bovine cell line with the compounds and by evaluation of the compounds in germfree calves infected by virus as explained hereinbelow under "Virological Testing."

DETAILED DESCRIPTION OF THE INVENTION

The antiviral pharmaceutical method of this invention utilizes the compounds of Formula I in the treatment of living animals to suppress the pathological effects of viral infection.

Compounds representing the dialkanolamines and sulfur analogs encompassed by Formula I have the Formula Ia:

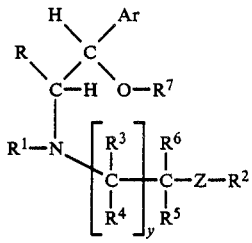

Formula $I_a$ wherein Ar, Z, R, $R^1$, $R^2$, $R^3$, $R^4$, $R^5$, $R^6$, $R^7$ and y are as defined under Formula I; and

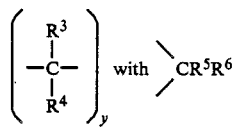

when taken together may form a lowercycloalkyl ring (3-9 carbons); and $R^5$ with $-ZR^2$ when taken together may form a 5-membered oxygen or sulfur heterocyclic ring, the stereoisomers thereof and the pharmaceutically acceptable acid addition salts thereof.

Compounds representing the 1,4-oxazine derivatives encompassed by Formula I have the Formula Ib:

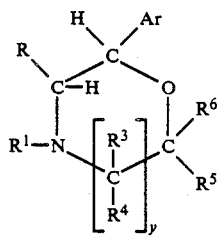

Formula $I_b$ wherein Ar, $R^1$, $R^3$, $R^4$, $R^5$, $R^6$ and y are as defined under Formula I; and

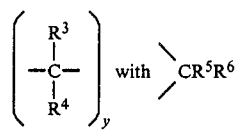

when taken together may form a lowercycloalkyl ring (3-9 carbons); the stereoisomers thereof, and the pharmaceutically acceptable acid addition salts thereof.

Compounds of Formula I wherein

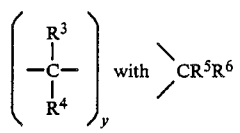

when taken together may form a lowercycloalkyl ring are illustrated by Formula Ic.

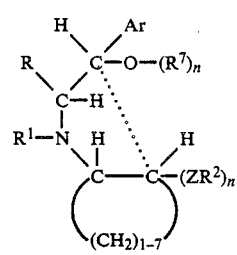

Formula $I_c$ wherein Ar, Z, R, $R^1$, $R^2$, $R^7$, and n are selected from values given under Formula I; the stereoisomers thereof, and the pharmaceutically acceptable acid addition salts thereof. See Example 35.

Compounds of Formula I wherein

with $(ZR^2)_n$ when taken together may form a 5-membered oxygen or sulfur heterocyclic ring are illustrated by Formula $I_d$.

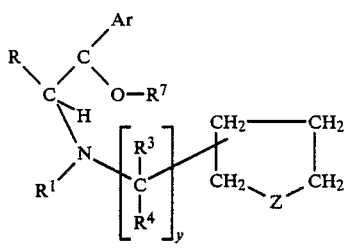

Formula $I_d$ wherein Ar, Z, R, $R^1$, $R^7$ and y are selected from values given under Formula I; the stereoisomers thereof, and the pharmaceutically acceptable acid addition salts thereof. See Example 30.

Compounds of Formula Ia wherein $R^7$ is hydrogen are prepared by methods illustrated by equations under Methods A and B as follows wherein the remainder of the symbols are as defined under Formula I:

METHOD A

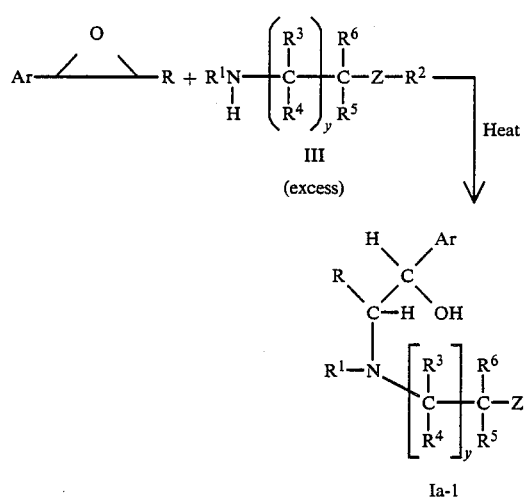

METHOD B

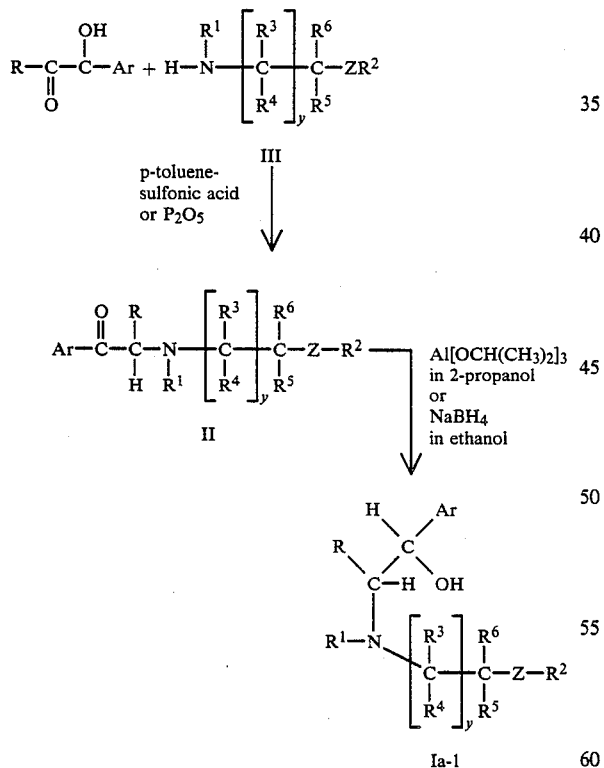

Compounds of Formula Ia wherein $R^6$ is other than hydrogen and $R^1$=H are prepared by Method C illustrated by equation as follows wherein remainder of the symbols are as defined under Formula I:

METHOD C

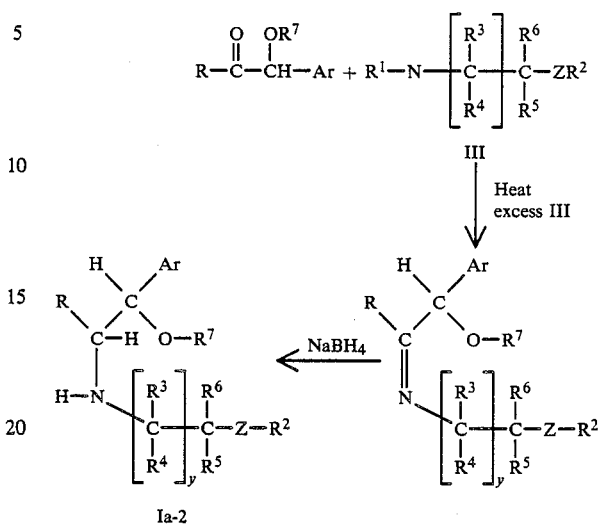

Compounds of Formula $I_b$ are prepared by Method D illustrated by the following equation wherein the symbols are as defined under Formula I:

METHOD D

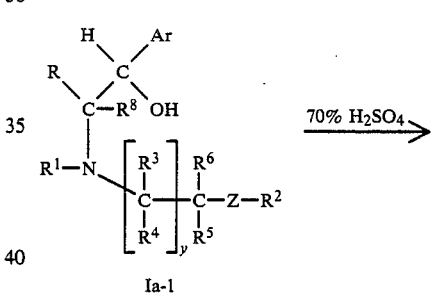

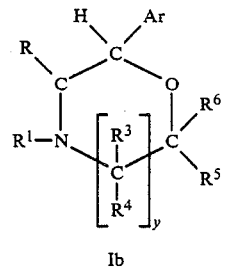

The oxides used in Method A may exist as trans and cis isomers which lead to stereo isomers (erythro and threo). Trans-stilbene oxide is available commercially. Trans-4,4-chlorostilbene oxide was prepared by the method described in ref. 1, page 2, (J. Am. Chem. Soc. 71, 478 (1949)). The corresponding cis stilbene oxide and cis-stilbene (phenyl substituted) oxides may be prepared by oxidizing cis-stilbene with perbenzoic acid as described by Lynch, B. M. and Pausacker, K. H., in J. Chem. Soc. (1955), pp. 1525–1531.

The erythro and threo isomers may also be separated when they exist together as a result of, for example, in Method B. See Example 20 for the fractional crystallization separation technique.

Optically active epoxides may be prepared by the method of Lufs Castedo, et al., Tetrahedron Letters, Vol. 25, No. 11, pp. 1205–1208 (1984) which employs reaction of dichlorocarbene with tertiary β-ethanolamines which are converted into the corresponding epoxides in good yield and with >95% stereospecificity. The equations for preparing starting oxides wherein R=methyl are:

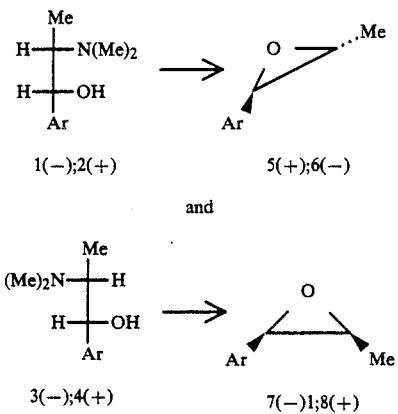

Unsymmetrical substituted benzoins needed for synthesis of amino ketones in Method B are readily obtained by cyanide-catalyzed reaction between two aromatic aldehydes having different substituents (Ide & Buck, Org. Reactions 4, 269 (1948) and J. Am. Chem. Soc. 53, 2350, 2784 (1931).

PREPARATION 1

2-[[1,2-bis(4-Chlorophenyl)-2-oxoethyl]amino]ethanol hydrochloride.

This material is the combined product of two separate batches.

I. In a closed system equipped with a Dean-Stark trap, a stirred solution of 4,4-dichlorobenzoin (10.0 g, 0.0357 mole), ethanolamine (2.35 g, 0.0385 mole), and a catalytic amount of p-toluenesulfonic aid in 250 ml toluene was heated at reflux temperature for 4 hours and the azeotroped water was collected in the Dean-Stark trap. After cooling, the toluene solution was washed with water, dried over magnesium sulfate and concentrated to an oil. The oil was dissolved in ether, treated with excess ethereal hydrogen chloride and the salt collected under nitrogen. Upon trying to recrystalize the salt from 350 ml of isopropyl ether (necessary for complete solution), 500 ml isopropyl ether, a yellow solid was obtained from this solution which was identified as 4,4′-dichlorobenzil. The filtrate was concentrated to 50 ml and isopropyl ether added to the hot solution until a faint turbidity was obtained. On standing overnight, a white solid was obtained, m.p. 177°–182° C. Recrystallization of the white solid from methanol-isopropyl ether and from acetonitrile-methanol yielded only semisolid salts. These were triturated with methyl ethyl ketone and dried to give 2.04 g total, m.p. 188°–193° C. This material gave a satisfactory elemental analysis for the title compound.

II. A mixture of 4,4′-dichlorobenzoin (3.52 g, 0.0125 mole), ethanolamine (0.83 g, 0.0235 mole), and phosphorus pentoxide (0.10 g) was heated on a steam bath for 6 minutes with thorough mixing. After cooling, the reaction mixture was dissolved in ether and the ether solution decanted from the phosphorus pentoxide. The solution was treated with ethereal hydrogen chloride and the solid salt collected by filtration and washed with isopropyl ether. The solid was purified by trituration with acetonitrile. The white solid was collected, washed with isopropyl ether, and dried in a vacuum oven at 50° C. for two hours. The yield was 3.24 g (72%), m.p. 190°–193° C.

The products from reactions I and II were combined, recrystallized from 75 ml absolute ethanol—150 ml isopropyl ether, and the salt dried in a vacuum for 16 hours, m.p. 192°–194° C. The salt was recrystallized a second time from 50 ml absolute ethanol—105 ml isopropyl ether and the salt dried at room temperature in a vacuum oven for 6 hours, m.p. 193.5°–195° C. (197–199 reported)*.

*Lit. Reference: J.A.C.S. 71 478 (1949).

Analysis: Calculated for $C_{16}H_{16}NO_2Cl_3$: C, 53.28; H, 4.47; N, 3.88. Found: C, 53.00; H, 4.48; N, 3.99.

PREPARATION 2

2-[(1,2-Diphenyl-2-oxoethyl)amino]ethanol hydrochloride.

This reaction was repeated twice and the products combined. A mixture of benzoin (5.30 g, 0.0250 mole), ethanolamine (1.59 g, 0.026 mole), and phosphorus pentoxide (0.2 g) was heated on a steam bath for 6 minutes after the material began to fuse. After cooling, the mixture was dissolved in ether and the ether decanted from some insoluble materials. A TLC analysis showed the solution to contain some of the starting benzoin. The reaction was repeated and the ether solutions combined. The combined solution was extracted twice with 30 ml portions of 6N hydrochloric acid solution. The acid extracts were combined and basified with 6N sodium hydroxide solution. The product was extracted twice with 50 ml portions of methylene chloride. The methylene chloride extract was washed with water, dried over magnesium sulfate, and concentrated to yield 5.89 g of yellow oil. The oil was dissolved in 200 ml of diethyl ether, treated with ethereal hydrogen chloride solution, and the solid collected by filtration to yield 4.52 g of the salt (31.1%). Recrystallization from absolute ethanol-isopropyl ether yielded 3.08 g white salt, m.p. 187°–188° C.

Analysis: Calculated for $C_{16}H_{18}NO_2Cl$: C, 65.86; H, 6.22; N, 4.80. Found: C, 65.53; H, 6.22; N, 4.92.

PREPARATION 3

2-(4-Dimethylaminophenyl)-2-(hydroxyethylamino)acetophenone.

(Tautomeric with 2-(Hydroxyethylimino)-2-[4-(dimethylaminophenyl)]-1-phenylethanol).

Ethanolamine, 6.1 g (0.10 mole) and 2.55 g (0.010 mole) of 2-hydroxy-2-phenyl-1-(4-dimethylamino)-phenylethanone were mixed and heated together at 105° C. under a stream of nitrogen for 16 hr. The reaction mixture was dissolved in 20 ml of hot methanol and the solution cooled to give 0.44 g of (first crop) white precipitate, which was shown by NMR analysis to be predominantly the title product, m.p. 162°–165° C. The filtrate was poured into 100 ml of water which resulted in separation of yellow-orange oil. The oil was separated and triturated with 50 ml toluene. The toluene solution was decanted away from a small amount of clear insoluble liquid. The toluene was removed on a rotary evaporator and the residual material triturated with acetone to give a yellow solid. Mass spectral analysis showed the solid to be the title compound and a component of mass 339 which would correspond to 1,2-bis-hydroxyimino-1-phenyl-2-(4-dimethylamino)-phenylethane. The impure solid was triturated with methanol-isopropyl ether mixture and the mixture subjected to filtration. The resulting solid second crop, 0.41 g, was yellow but melted at same temperature 162°–165° C. as the first crop. Total yield was 0.85 g (29%).

PREPARATION 4

1,2-Diphenyl-2-methoxy-1-(2-hydroxyethylimino)ethane.

Ethanolamine, 8.34 g (0.137 mole) and 4.52 g (0.020 mole) of 2-methoxy-1,2-diphenylethanone were mixed together and heated at 120° C. under a gentle stream of nitrogen for 2 hr. Mass spec analysis indicated none of the 2-methoxy-1,2-diphenylethanone remained. The mixture stood at ambient temperature for 16 hr, after which it was dissolved in 20 ml of methanol. The solution was poured into 100 ml of water. A yellow oil separated which became semisolid after 1 hr. The semisolid was extracted twice with 50 ml portions of methylene chloride. The extract was dried over magnesium sulfate, filtered, and concentrated to give 5.04 g of yellow oil (94%) which began to solidify on standing. Trituration with petroleum ether gave 2.19 g of off-white solid after filtration. The filtrate was concentrated to give an additional 2.25 g of yellow oil which was identical to the white solid and which crystallized on standing.

PREPARATION 5

2-[(2-Methoxyethyl)amino]-1-phenyl-1-propanone, monohydrochloride.

A solution of α-bromopropiophenone (2.13 g, 0.010 mole) in ether (10 ml) was added dropwise to a stirred solution of 2-methoxyethylamine (1.50 g, 0.020 mole) in ether (20 ml). The mixture was then stirred at ambient temperature for 18 hr. The ether layer was decanted from an insoluble oil, washed with water (20 ml), and then extracted with 2N hydrochloric acid solution (20 ml). The acid extract was basified to pH 10 with 6N sodium hydroxide solution, and this solution extracted with ether (50 ml). The extract was dried over magnesium sulfate and concentrated to give a clear yellow oil. The oil was dissolved in ether and treated with excess ethereal hydrogen chloride. The product separated from solution as an oil, but solidified upon trituration. The yield was 0.85 g (35%), m.p. 133°–134° C.

Analysis: Calculated for $C_{12}H_{17}NO_2 \cdot HCl$: C, 59.14; H, 7.44; N, 5.75. Found: C, 59.13; H, 7.66; N, 5.77.

EXAMPLE 1

4-Chloro-α-(4-chlorophenyl)-β-[2-(hydroxyethyl)amino]benzeneethanol, erythro isomer, hydrochloride.

A mixture of trans-4,4'-dichlorostilbene oxide (5.30 g, 0.202 mole) and ethanolamine (3.66 g, 0.06 mole) was heated at 125°–130° C. in an oil bath for 30 minutes. After cooling, the mixture was dissolved in toluene and washed with water to remove unreacted ethanolamine. The toluene solution was dried over magnesium sulfate and concentrated at reduced pressure. The residual oil crystallized on standing. The solid was recrystallized from toluene-isooctane to yield 8.61 g white solid. The solid was dissolved in methylene chloride, washed with water, dried over magnesium sulfate, and concentrated to an oil which crystallized on standing. The solid was dissolved in ether (large volume required) and treated with ethereal hydrogen chloride solution. The salt could not be collected by filtration due to small particle size. The ether was allowed to evaporate overnight and the residual solid material recrystallized from absolute ethanol-isopropyl ether to give 41.6 g white salt (57.4%), m.p. 240°–243° C.

Analysis: Calculated for $C_{16}H_{18}NO_2Cl_3$: C, 52.99; H, 5.00; N, 3.86. Found: C, 52.97; H, 5.02; N, 3.92.

Lit. Reference: J.A.C.S. 71, 478 (1949).

EXAMPLE 2

β-[(2-Hydroxyethyl)amino]-α-phenylbenzeneethanol, erythro isomer, hydrochloride.

This material was the combined product of two reactions.

I. A mixture of trans-stilbene oxide (3.93 g, 0.020 mole) and ethanolamine (3.66 g, 0.06 mole) was stirred while being heated at 120°–130° C. for 1 hr. The initial melt gave 2 layers which became a homogenous clear yellow liquid within 30 minutes. The mixture was dissolved in toluene (50 ml), washed twice with 15 ml portions of water, and dried over magnesium sulfate. After standing a few minutes the product precipitated from the toluene. Methanol was added to dissolve the product, and the drying agent removed by filtration. The filtrate was concentrated to yield 4.04 g white solid (78.6%). Recrystallization from toluene (20 ml) gave 3.63 g white solid, the free base of the title compound.

II. Procedure was the same as I except the quantities were doubled. The yield of free base was 94.6%. The free bases from this and I were combined, dissolved in 50 ml methanol, treated ith excess ethereal hydrogen chloride, diluted with ether and the salt collected under nitrogen to yield 13.31 g, m.p. 241°–242° C.

Analysis: Calculated for $C_{16}H_{20}NO_2Cl$: C, 65.41; H, 6.86; N, 4.77. Found: C, 65.40; H, 6.89; N, 4.77.

Lit. Reference: J.A.C.S. 70 2015 (1948).

EXAMPLE 3

4-Chloro-α-(4-chlorophenyl)-β-[(2-mercaptoethyl)amino]benzeneethanol, hydrochloride.

A mixture of trans-4,4'-dichlorostilbene oxide (5.30 g, 0.020 mole), 2-aminoethanethiol hydrochloride (6.81 g, 0.06 mole), and triethylamine (20 ml) was stirred and heated at 125° C. in an oil bath for 20 hours. After cooling, the triethylamine was decanted off. The residual material was dissolved in a little methanol, diluted with 300 ml water, and basified to pH 10 with 6N sodium hydroxide solution. The insoluble material was collected and washed with water. The dried solid was shown by NMR analysis to contain product and 15–20% 4,4'-dichlorostilbene oxide. Trituration of the crude product with various solvents did not remove the impurity. It was found that the product was less soluble than the impurity in ether. By trituration with small volumes of ether and slow partial evaporation and chilling, 1.88 g pure product (27.5%) was obtained. Of this material, 1.73 g was dissolved in 400 ml ether and treated with excess ethereal hydrogen chloride to form 1.85 g of the hydrochloride salt. Recrystallization from absolute ethanol-isopropyl ether gave 1.72 g of the salt, m.p. 205°–206° C.

Analysis: Calculated for $C_{16}H_{18}NOSCl_3$: C, 50.74; H, 4.79; N, 3.70. Found: C, 50.47; H, 4.78; N, 3.74.

EXAMPLE 4

β-[(2-Mercaptoethyl)amino]-α-phenylbenzeneethanol, hydrochloride.

A stirred mixture of trans-stilbene oxide (6.15 g, 0.0314 mole), 2-aminoethanethiol hydrochloride (3.57 g, 0.0314 mole) and triethylamine was heated at 120° C. for 18 hours. After cooling, the partially solidified reaction mixture was dissolved in methanol (50 ml) and diluted with 300 ml water. The solid that precipitated was collected by filtration to give 6.19 g impure white solid which was determined by NMR analysis to be a mixture of 40% product/60% stilbene oxide. After the filtrate stood overnight, 0.67 g pure product was collected.

The impure solid, an additional 7.14 g (0.0628 mole) 2-aminoethanethiol hydrochloride and 20 ml triethylamine was stirred and heated at 120° C. for two hours and then worked up as before. The solid obtained still contained 15% stilbene oxide. This solid was combined with the 0.67 g pure product previously isolated, dissolved in methanol, treated with excess ethereal hydrogen chloride diluted with ether, and the solid salt collected under nitrogen to yield 8.06 g white solid salt (82.8%). Recrystallization from methanol-isopropyl ether yielded 2.64 g of solid. An additional 0.51 g was obtained by evaporating the filtrate and recrystallizing the remaining gummy solid from a small volume of methanol-isopropyl ether.

Analysis: Calculated for $C_{16}H_{20}NOSCl$: C, 62.02; H, 6.51; N, 4.52. Found: C, 61.70; H, 6.55; N, 4.55.

EXAMPLE 5

α-[(3-Hydroxypropyl)amino]phenylmethyl]benzenemethanol, erythro isomer, hydrochloride.

A mixture of trans-stilbene oxide (7.86 g, 0.04 mole) and propanolamine (9.02 g, 0.12 mole) was stirred while being heated at 120°-130° C. for 1 hr. The initial melt gave 2 layers which became a homogenous clear yellow liquid within 30 minutes. The mixture was dissolved in chloroform (150 ml), washed twice with 15 ml portions of water, and dried over magnesium sulfate. After standing a few minutes the product precipitated from the chloroform. Methanol was added to dissolve the product and the drying agent removed by filtration. Ethereal hydrogen chloride was added in excess to the filtrate and the mixture was diluted with ether. The salt was collected and dried under nitrogen to yield 10.2 g (83%), m.p. 197°-198° C.

Analysis: Calculated for $C_{17}H_{21}NO_2 \cdot HCl$: C, 66.33; H, 7.20; N, 4.55. Found: C, 66.44; H, 7.25; N, 4.56.

EXAMPLE 6

β-[(2-Hydroxypropyl)amino]-α-phenylbenzeneethanol.

A mixture of trans-stilbene oxide (3.93 g, 0.20 mole) and 1-amino-2-propanol (4.51 g, 0.060 mole) was heated in an oil bath at 125° C. for 1 hour. After standing at ambient temperature for 18 hours, the viscous oil was dissolved in 20 ml of methanol and diluted with water causing a white solid to precipitate. The solid was collected, washed with water, and dried under ambient conditions to give 4.57 g (84%) of the product which was recrystallized from toluene to give 3.65 g solids; m.p. 116°-118° C.

Analysis: Calculated for $C_{17}H_{21}NO_2$: C, 75.75; H, 7.80; N, 5.16. Found: C, 75.21; H, 7.87; N, 5.15.

EXAMPLE 7

β-[(2-Ethoxyethyl)amino]-α-phenylbenzeneethanol.

A mixture of trans-stilbene oxide (1.96 g, 0.010 mole) and 2-ethoxyethylamine (2.67 g, 0.030 mole) was heated at 140° C. for 6 hours. After standing at ambient temperature for 10 hours, the solidified reaction mixture was triturated with isooctane and filtered to give 2.28 g of white solid (80%) which was recrystallized from isooctane, m.p. 128°-130° C.

Analysis: Calculated for $C_{18}H_{23}NO_2$: C, 75.76; H, 8.12; N, 4.91. Found: C, 75.73; H, 8.20; N, 4.89.

EXAMPLE 8

β-[(2-Methoxyethyl)amino]-α-phenylbenzeneethanol.

A mixture of trans-stilbene oxide (3.93 g, 0.020 mole) and 2-methoxyethylamine (4.51 g, 0.060 mole) was heated at 125° C. for 2 hours with an oil bath. A mass spectra analysis showed no title compound was present. The mixture was heated for another 2 hours at 150° C. The mixture was poured into water (using methanol rinse) to obtain an off-white solid. NMR analysis showed the solid contained approximately 60% unreacted stilbene oxide. The mixture was added to another 4.51 g (0.060 mole) of 2-methoxy ethylamine and the mixture heated at 135° C. for 4 hours in a stainless-steel bomb. After cooling, the reaction mixture was shown by NMR analysis to contain 20% stilbene oxide and 80% of the title compound. The solid was recrystallized from toluene to give 2.92 g (54%) of a white solid, m.p. 137°-139° C.

Analysis: Calculated for $C_{17}H_{21}NO_2$: C, 75.25; H, 7.80; N, 5.16. Found: C, 75.28; H, 7.81; N, 5.12.

EXAMPLE 9

β-[(2-Hydroxyethyl)methylamino]-α-phenylbenzeneethanol, monohydrochloride, hemihydrate.

A mixture of trans-stilbene oxide (3.96 g, 0.020 mole) and N-methylethanolamine (4.51 g, 0.060 mole) was heated at 125° C. for 18 hours. The mixture was then dissolved in 20 ml of methanol and the solution poured into 150 ml of water, causing a heavy cream-colored oil to separate from solution. The mixture was extracted with 2×100 ml portions of methylene chloride. The combined extract was dried over magnesium sulfate and concentrated to give 5.62 g (100%) of an oil. The oil was dissolved in ether and treated with excess ethereal hydrogen chloride solution. The ether was decanted and the oil treated with isopropyl ether to give a solid. The solid was collected by filtration and vacuum dried at 40°-60° C. for 28 hours, m.p. 69°-80° C.

Analysis: Calculated for $C_{17}H_{21}NO_2 \cdot HCl \cdot 0.5H_2O$: C, 64.45; H, 7.32; N, 4.42. Found: C, 64.94; H, 7.43; N, 4.60.

EXAMPLE 10

α-[[(5-Hydroxypentyl)amino]phenylmethyl]benzenemethanol, erythro isomer, monohydrochloride.

A mixture of 6.4 g (0.06 mole) of 5-amino-1-pentanol and 12.7 g (0.06 mole) of benzoin was heated to form a yellow solution. The melt was heated at 100°-105° C. for four hours and reaction was complete as followed by CI mass spectrometry. The reaction mixture was cooled and dissolved in 30 ml of absolute ethanol. The ethanol solution was added in a fine stream to a solution of 4.4 g (0.12 mole) of sodium borohydride dissolved in 34 ml of 50% ethanol-water.

When the addition was complete, some solid was undissolved. Tetrahydrofuran (20 ml) was added to give a complete solution. The product precipitated from solution after stirring at ambient temperature for two hours. The white solid was collected and the damp filter cake was added to 70 ml of 2N sodium hydroxide and 70 ml of toluene. The mixture was stirred for one hour. The solid was collected and dried to give 12.1 g (67%) of product as the free base. The 12.1 g of free base was dissolved in 60 ml of isopropanol and acidified with 6N methanolic hydrogen chloride. The hydrochloride salt was collected to yield 10.7 g of solid. m.p. 127°–136° C. The crude material was recrystallized twice from isopropanol-isopropyl ether to give 9.1 g solid, m.p. 134°–136° C. $C^{13}$ NMR spectrum was consistent for the erythro isomer.

Analysis: Calculated for $C_{19}H_{26}ClNO_2$: C, 67.95; H, 7.80; N, 4.17. Found: C, 67.57; H, 7.83; N, 4.10.

EXAMPLE 11

α-[[(6-Hydroxyhexyl)amino]phenylmethyl]benzenemethanol, erythro isomer, monohydrochloride.

A mixture of 7.0 g (0.06 mole) of 6-amino-1-hexanol and 12.7 g (0.06 mole) of benzoin was heated to form a yellow solution. The solution was heated at 100°–105° C. for four hours then cooled and dissolved in 30 ml of absolute ethanol and 50 ml of tetrahydrofuran. The solution was added in a fine stream to a solution of 4.4 g (0.12 mole) of sodium borohydride dissolved in 34 ml of 50% ethanol-water. The solution was stirred at ambient temperature for three hours then concentrated to a light yellow solid. The residue was added to 70 ml of 2N sodium hydroxide and 70 ml toluene. The mixture was stirred for one hour and the resulting solid was collected to give 18.4 g of free base of title compound (99%). The free base was dissolved in 55 ml of isopropanol and the solution acidified with 6N methanolic hydrogen chloride. The solution was concentrated to a syrup which crystallized on standing. Two recrystallizations from isopropanol-isopropyl ether gave 12.5 g of solid (60%), m.p. 142°–144° C. $C^{13}$NMR spectrum was consistent for the erythro isomer.

Analysis: Calculated for $C_{20}H_{28}ClNO_2$: C, 68.65; H, 8.07; N, 4.00. Found: C, 68.46; H, 8.11; N, 3.95.

EXAMPLE 12

β-[(3-Hydroxypropyl)amino]-4-methoxy-α-(4-methoxyphenyl)benzeneethanol, monohydrochloride, hemihydrate.

A mixture of anisoin (10.0 g, 0.037 mole), 3-propanolamine (11.03 g, 0.147 mole) and phosphorus pentoxide (2.5 g, 0.018 mole) was heated for 4 hours in an oil bath at 105° C. with nitrogen purge. Water was produced and evaporated as the reaction proceeded to completion. The reaction mixture was cooled and chloroform (100 ml) added. The chloroform layer was washed with dilute acid (100 ml×2). The aqueous washes were combined, made basic and washed with chloroform. The organic layer was concentrated and dissolved in 100 ml of ethanol to which solution an aqueous solution of sodium borohydride (0.074 mole) was added. The resulting mixture was stirred for 1.5 hr. The mixture was concentrated to dryness and the residue was partitioned between 100 ml of 25% aqueous sodium hydroxide solution and 500 ml methylene chloride. The methylene chloride layer was washed with water (2×100 ml), concentrated and the concentrate was dissolved in hot isopropyl alcohol. A solution of hydrogen chloride in isopropyl alcohol was added. The precipitate was collected by filtration and suspended in acetone, filtered off and dried to give 5.19 g (36.5%) of the hydrochloride salt, m.p. 157°–159° C.

Analysis: Calculated for $C_{19}H_{27}O_{4.5}NCl$: C, 60.56; H, 7.21; N, 3.72. Found: C, 60.53; H, 7.04; N, 3.69.

EXAMPLE 13

β-[(5-Hydroxypentyl)amino]-4-methoxy-α-(4-methoxyphenyl)benzeneethanol fumarate hemihydrate.

A mixture of anisoin (10.0 g, 0.037 mole), 5-amino-1-pentanol (11.37 g, 0.11 mole) and phosphorus pentoxide (2.5 g, 0.018 mole) was heated for 4 hours in an oil bath at 105° C. with a nitrogen purge. Water was produced and evaporated as the reaction proceeded to completion. The reaction mixture was cooled and chloroform (100 ml) added. The chloroform layer was washed with dilute acid (100 ml×2). The aqueous washes were combined, made basic and washed with chloroform. The organic layer was concentrated and dissolved in 100 ml of ethanol, to which solution an aqueous solution of sodium borohydride (0.074 mole) was added. The resulting mixture was stirred for 1.5 hr and concentrated to dryness. The residue was partitioned between 100 ml of 25% sodium hydroxide and 500 ml of methylene chloride. The methylene chloride layer was washed with water (2×100 ml), concentrated and the concentrate was dissolved in methyl isobutylketone. Fumaric acid (0.037 mole) was added. The precipitate was recrystallized in acetone, filtered off and dried to give 7.09 g (52.9%) of crystals, m.p. 172°–175° C.

Analysis: Calculated for $C_{25}H_{34}N_1O_{8.5}$: C, 61.97; H, 7.07; N, 2.89. Found: C, 61.72; H, 6.92; N, 2.96.

EXAMPLE 14

β-[(6-Hydroxyhexyl)amino]-4-methoxy-α-(4-methoxyphenyl)benzene ethanol, erythro isomer, monohydrochloride.

A mixture of 4.7 g (0.039 mole) of 6-amino-1-hexanol and 11.2 g (0.039 mole) of anizoin was heated to form a yellow solution. The solution was heated at 100°–105° C. for 4 hrs then cooled and dissolved in 30 ml of 200 proof ethanol and 20 ml of tetrahydrofuran. The solution was added in a fine stream to a solution of 3.0 g (0.08 mole) of sodium borohydride dissolved in 17 ml of 200 proof ethanol and 17 ml of water. The solution was stirred at ambient temperature for five hours then concentrated to a yellow gum. The residue was partitioned between 70 ml of 2N sodium hydroxide and 70 ml of toluene. The toluene layer was separated and washed with water. The toluene solution was dried over type 3A molecular sieve powder. After filtration, the filtrate was concentrated to 10 g of yellow, viscous liquid. The residue was dissolved in 30 ml of isopropanol and acidified with 6N methanolic hydrogen chloride. The hydrochloride salt crystallized to give 6 g of crystals, m.p. 118°–121° C. Two recrystallizations from isopropanolisopropyl ether gave 2.9 g of crystals, m.p. 125°–127° C. $C^{13}$NMR spectrum was consistent for the erythro isomer.

Analysis: Calculated for $C_{22}H_{32}ClNO_4$: C, 64.46; H, 7.87; N, 3.42. Found: C, 64.12; H, 7.92; N, 3.42.

EXAMPLE 15

β-[(4-Hydroxybutyl)amino]-α-phenylbenzeneethanol, erythro isomer, monohydrochloride.

A mixture of 5.4 g (0.056 mole) of 4-amino-1-butanol and 11.0 g (0.056 mole) of benzoin was heated to form a yellow solution. The solution was heated at 100°–105° C. for two hours then cooled and dissolved in 30 ml of absolute ethanol. The ethanol solution was added in a fine stream to a solution of 4.2 g (0.112 mole) of sodium borohydride dissolved in 34 ml of 50% ethanol-water. The solution was stirred for two hours then concentrated to a syrup which crystallized on cooling. The residue was stirred with 75 ml of 2N sodium hydroxide and 75 ml of toluene to give 12.2 g (76%) of product as the free base.

The free base was dissolved in 50 ml of isopropanol and acidified with 6N methanolic hydrogen chloride to give 7.5 g of hydrochloride salt, m.p,. 164°-170° C. Two recrystallizations from isopropanol-isopropylether gave 2.9 g of crystals, m.p. 175°-177° C. $C^{13}$NMR spectrum was consistent for the erythro isomer.

Analysis: Calculated for $C_{18}H_{24}ClNO_2$: C, 67.17; H, 7.52; N, 4.35. Found: C, 67.16; H, 7.82; N, 4.35.

EXAMPLE 16

β-[(2-Hydroxy-1-methylethyl)amino]-α-phenylbenzeneethanol.

A mixture of trans-stilbene oxide (3.93 g, 0.020 mole) and 2-amino-1-propanol (4.51 g, 0.060 mole) was heated on a steam bath for 18 hours. The reaction mixture was dissolved in methanol (20 ml) and the solution poured into water (200 ml). The viscous oil which separated from the solution crystallized on standing. The solid was collected to obtain 4.29 g (79%) of material which was recrystallized from toluene to give 3.36 g of a white solid. The solid was dried in vacuo for 2 hours, m.p. 104°-105° C.

Analysis: Calculated for $C_{17}H_{21}NO_2$: C, 75.25; H, 7.80; N, 5.16. Found: C, 75.30; H, 7.86; N, 5.23.

EXAMPLE 17

α-[[(2-Methoxyethyl)amino]methyl]benzenemethanol.

A mixture of styrene oxide (2.40 g 0.030 mole) and 2-methoxyethylamine (4.50 g, 0.060mole) was heated on a steam bath for 16 hours. After cooling to ambient temperature the oil began to crystallize. Trituration in isooctane followed by filtration gave a slightly impure solid. Recrystallization from isopropyl ether gave 1.52 g (39%) of the product, mp 77°-80° C.

Analysis: Calculated for $C_{11}H_{17}NO_2$: C, 67.66; H, 8.78; N, 7.17. Found: C, 67.42; H, 8.87; N, 7.15.

EXAMPLE 18

β-[(4-Hydroxybutyl)amino]-4-methoxy-α-(4-methoxyphenyl)benzeneethanol, monohydrochloride, hemihydrate.

A mixture of anisoin (10.0 g, 0.037 mole), 4-amino-1-butanol (6.59 g, 0.074 mole) and phosphorus pentoxide (2.5 g, 0.018 mole) was heated for 5 hours in an oil bath at 105° C. with a nitrogen purge. After the reaction was complete the mixture was worked up as in Example 12. The hydrochloride salt was recrystallized in acetone/isooctane and the crystals filtered off, dried, and analyzed (3.0 g, 27.0%), m.p. 114°-117° C.

Analysis: Calculated for $C_{20}H_{29}N_1O_{4.5}Cl_1$: C, 61.45; H, 7.48; N, 3.58. Found: C, 60.97; H, 7.32; N, 3.78.

EXAMPLE 19

β-[(2-Hydroxyethyl)amino]-4-methoxy-α-(4-methoxyphenyl)benzeneethanol, monohydrochloride, sesquihydrate.

A mixture of anisoin (20.0 g, 0.074 mole), 2-aminoethanol (13.54 g, 0.22 mole) and phosphorus pentoxide (2.5 g, 0.018 mole) was heated for 4 hrs in an oil bath at 105° C. with a nitrogen purge. After the reaction was complete, the work-up process was identical to the procedure for Example 12. The hydrochloride salt was recrystallized in hot dimethyl ether/methanol (100:5) and the crystals were filtered off and dried to give 3.53 g (14.0%) of title compound, m.p. 204°-206° C.

Analysis: Calculated for $C_{18}H_{27}H_{27}NO_{5.5}Cl$: C, 56.77; H, 7.15; N, 3.68. Found: C, 57.01; H, 6.60; N, 3.74.

EXAMPLE 20

β-[(2-Hydroxyethyl)amino]-α-phenylbenzeneethanol, threo isomer, monohydrochloride.

Benzoin, 3.6 kg (17.0 mole) was reacted with 1.14 kg (18.7 mole) of ethanolamine at 100°-105° C. for 2 hr. The reaction mixture was dissolved in a mixture obtained by mixing 17 liters of absolute ethanol and 1.285 kg (34.0 moles) of sodium borohydride dissolved in 5 liters of water. After 2 hrs, the reaction was complete giving a mixture of erythro and threo isomers of β-[(2-hydroxyethyl)amino]-α-phenylbenzeneethanol. Solvents were evaporated to give an amber colored syrup. The syrup was partitioned between 6 liters of toluene and 6.4 liters of 25% sodium hydroxide. At this point, 3.15 kg of the erythro isomer crystallized from the two phase mixture and was separated by filtration. The toluene layer from the filtrate was separated from the aqueous layer and acidified to pH 2 with 9N methanolic hydrochloric acid. The solid which precipitated was vacuum dried to give 272 g of a mixture of the hydrochloride salt of the erythro and threo isomers. The salt was partitioned between toluene and 50% aqueous sodium hydroxide solution. The toluene layer was separated and 101 g of a white solid crystallized from the solution, NMR analysis showed it to be 70% erythro and 30% threo isomers free base. A sample, 10 g, of the free base was dissolved in 30 ml of hot isopropyl alcohol and the solution was acidified with 4N hydrochloric acid. The white crystals, 5.9 g, obtained by filtration were identified as the erythro isomer, hydrochloride. The filtrate was stripped yielding 4.42 g solid identified as a mixture containing 90% threo- and 10% erythro isomer hydrochlorides. A portion of the mixture, 3.44 g, was dissolved in hot isopropyl alcohol. The solution was cooled and left to crystallize overnight. The crystalline product collected by filtration was mainly the erythro isomer salt. The filtrate was concentrated to give 1.72 g crystals, mainly the threo isomer salt containing an estimated 2-3% of the erythro isomer salt. Recrystallization of the last crystals in methanol-isopropyl alcohol (1:10) gave 1.30 g of white crystalline powder, m.p. 188°-190° C.

Analysis: Calculated for $C_{16}H_{20}O_2NCl$: C, 65.41; H, 6.86; N, 4.77. Found: C, 65.25; H, 6.96; N, 4.75.

EXAMPLE 21

4-(Dimethylamino)-β-[(2-hydroxyethyl)amino]-α-phenylbenzeneethanol.

Sodium borohydride (0.22 g, 0.0057 mole) was added in several portions to a stirred suspension of 2-(4-dimethylaminophenyl)-2-(hydroxyethylamino)acetophenone (0.85 g, 0.00285 mole) in 50 ml of absolute ethanol and the mixture stirred at ambient temperature for 0.5 hr. The mixture was then heated to reflux temperature for 0.5 hr, cooled to ambient temperature, and 6N HCl solution added until the mixture was neutral. The mixture was concentrated to give a yellow solid. This solid was dissolved in a minimum volume of methanol and acidified with 6N hydrochloric acid to give a clear yellow solution. This solution was brought to pH 8 with 6N sodium hydroxide solution, cooled by the addition of ice, and the white solid collected to obtain 0.54 g (63%) of the desired product. Recrystallization from acetoneisopropyl ether gave 0.25 g of title compound, m.p. 147°–148° C.

Analysis: Calculated for $C_{18}H_{24}N_2O_2$: C, 71.97; H, 8.05; N, 9.33. Found: C, 71.99; H, 8.09, N, 9.32.

EXAMPLE 22

2-[(2-Methoxy-1,2-diphenylethyl)amino]ethanol, monohydrochloride.

Sodium borohydride (1.25 g, 0.033 mole) was added in small portions to a stirred suspension of 1,2-diphenyl-2-methoxy-1-(2-hydroxyethylimino)ethane (4.44 g, 0.016 mole) in 50 ml of absolute ethanol. After the addition of the sodium borohydride was completed, the mixture was stirred at ambient temperature for 0.5 hr and heated at refluxed temperature for 1 hr. The reaction mixture was stirred at ambient temperature for 16 hr. The reaction mixture was treated with 6N hydrochloric acid solution carefully to destroy excess sodium borohydride and acidified to pH 3. Then the mixture was brought to pH 8 by addition of 6N sodium hydroxide solution and diluted to a volume of 200 ml with water. The mixture was extracted with 2×75 ml portions of methylene chloride. The extract was dried over magnesium sulfate and concentrated to obtain 4.07 g (41% yield) of a clear oil, the free base of the title compound. The oil was dissolved in ether (100 ml) and the solution treated with excess ethereal hydrogen chloride solution to form the hydrochloride salt (3.46 g). The hydrochloride salt was recrystallized from absolute ethanol-isopropyl ether, m.p. 220°–222° C.

Analysis: Calculated for $C_{17}H_{22}NO_2Cl$: C, 66.33; H, 7.20; M, 4.55. Found: C, 66.21; H, 7.25; N, 4.57.

EXAMPLE 23

α-[[(2-Hydroxyethyl)amino]methyl]benzenemethanol.

A mixture of styrene oxide (2.40 g, 0.020 mole) and ethanolamine (1.22 g, 0.020 mole) was heated at 125° C. in an oil bath for 2 hr. An NMR analysis showed no styrene oxide remaining. On standing at ambient temperature for 16 hrs, partial solidification occurred. The material was triturated with ethyl acetate, giving a white solid which was collected by filtration and washed with isopropyl ether. A small amount of second crop was obtained from the filtrate for a total of 0.82 g (23%). Recrystallization from ethyl acetate-isopropyl ether gave 0.69 g of a white solid, m.p. 96°–98° C.

Analysis: Calculated for $C_{10}H_{15}NO_2$: C, 66.27; H, 8.34; N, 7.73. Found: C, 66.36; H, 8.41; N, 7.74.

EXAMPLE 24

4-Chloro-α-(4-chlorophenyl)-β-[(2-hydroxyethyl)amino]benzeneethanol, monohydrochloride, hemihydrate.

A mixture of 90% pure 4,4'-dichlorobenzoin (10.0 g, 0.036 mole) and 3-propanolamine (2.70 g, 0.036 mole) was heated for 4 hrs in an oil bath at 105° C. with a nitrogen purge. After the reaction was complete, the contents were cooled and chloroform (100 ml) added. The organic layer was washed with dilute acid then the acidic layer neutralized and washed with chloroform. The organic layer was concentrated and dissolved in ethanol (100 ml) to which an aqueous solution of sodium borohydride (0.074 mole) was added. The reaction mixture was stirred 1.5 hr, then concentrated to dryness. The yellow solid was partitioned between 25% aqueous sodium hydroxide (100 ml) and methylene chloride (200 ml). The organic layer was washed with water (2×100 ml) concentrated and the residue dissolved in hot isopropyl alcohol. A hydrogen chloride/isopropyl alcohol solution was added. Crystals were filtered off and redissolved in hot acetone/isooctane. The solution was cooled and the crystals were filtered off and recrystallized from methyl isobutylketone to give 1 g of solids (26.6%), m.p. 176°–180° C.

Analysis: Calculated for $C_{17}H_{21}O_{2.5}NCl_3$: C, 52.94; H, 5.49; N, 3.63. Found: C, 48.15; H, 4.75; N, 3.31.

EXAMPLE 25

β-[[3-(1-Methylethoxy)propyl]amino]-α-phenylbenzeneethanol.

A mixture of trans-stilbene oxide (1.96 g, 0.010 mole) and 3-isopropoxy-1-propylamine (3.51 g, 0.030 mole) was heated at 140° C. for 5 hrs. After standing at ambient temperature for 18 hrs the mixture was dissolved in acetone (20 ml) and the solution poured into water (120 ml). A solid formed rapidly and was collected by filtration and dried at ambient temperature. The solid (2.80 g, 89%) was recrystallized from toluene-isooctone to yield 2.08 g of a fluffy white solid, m.p. 106°–108° C.

Analysis: Calculated for $C_{20}H_{27}N_2O_2$: C, 76.64; H, 8.68; N, 4.47. Found: C, 76.64; H, 8.87; N, 4.46.

EXAMPLE 26

β-[[3-(2-Methylpropoxy)propyl]amino]-α-phenylbenzeneethanol.

A mixture of trans-stilbene oxide (91.96 g, 0.10 mole) and 3-isobutoxy-1-propylamine (3.93 g, 0.030 mole) was heated at 140° C. for 5 hrs. After standing at ambient temperature for 18 hrs the mixture was dissolved in acetone (20 ml) and the solution poured into water (120 ml). A solid formed rapidly which was collected by filtration and dried under ambient conditions to obtain 2.89 g (88%) of the desired product. Recrystallization from tolueneisooctone gave 2.44 g of an off-white solid, m.p. 90°–92° C.

Analysis: Calculated for $C_{21}H_{29}NO_2$: C, 77.02; H, 8.93; N, 4.28. Found: C, 77.07; H, 9.05; N, 4.23.

EXAMPLE 27

β-[(2-Hydroxyethyl)amino]-4-methyl-α-(4-methylphenyl)benzene-ethanol, monohydrochloride.

A mixture of 40.0 g (0.33 mole) of tolualdehyde, 10 ml ethanol and 10.84 g (0.17 mole) of potassium cyanide was refluxed overnight at 90° C. An additional 10.8 g (0.17 mole) of potassium cyanide was added and the mixture was refluxed for 5 hr more. Aqueous sodium bisulfite was added to remove unreacted aldehyde. The mixture was reheated, cooled and extracted with methylene chloride. The solvent was stripped off. On dissolving the residue in isopropyl alcohol, crystals were obtained in amount of 14.26 g which represents a 35% yield of 4,4'-dimethylbenzoin. A portion of the 4,4'-dimethylbenzoin, 4.74 g (0.19 mole), 3.84 g (0.063 mole) of ethanolamine and 2.5 g (0.018 mole) of phosphorus pentoxide were mixed and heated under nitrogen atmosphere by means of an oil bath for 4 hr at 105° C. The reaction mixture was cooled and 100 ml of chloroform was added to it with mixing. The chloroform layer was separated and washed twice with 100 ml of dilute hydrochloric acid each time. The aqueous layers were combined, basified and washed with chloroform. The chloroform layer was separated, concentrated and dissolved in 100 ml of ethanol to which 0.038 mole of sodium borohydride in aqueous solution was added. The mixture was stirred for 2 hr and concentrated to dryness. The residue was partitioned between 100 ml of 25% sodium hydroxide and 100 ml of methylene chloride. The methylene chloride layer was washed twice with 100 ml of water each time, concentrated and the residue was dissolved in hot isopropyl alcohol. A solution of hydrogen chloride in isopropyl alcohol was added to give, after filtration and drying, 1.25 g (48.8%) of the hydrochloride salt, m.p. 217°–220° C.

Analysis: Calculated for $C_{18}H_{24}NO_2Cl$: C, 67.17; H, 7.52; N, 4.35. Found: C, 66.83; H, 7.69; N, 4.32.

EXAMPLE 28

β-[(3-Butoxypropyl)amino]-α-phenylbenzeneethanol.

A mixture of trans-stilbene oxide (1.96 g, 0.010 mole) and 3-(n-butyloxy)-1-propylamine (3.93 g, 0.030 mole) was heated at 140° C. for 5 hrs. After standing at ambient temperature for 18 hr, the mixture was dissolved in acetone (20 ml) and the solution poured into water (120 ml). The solid which formed was collected by filtration and dried under ambient conditions to yield 3.24 g of slightly wet solid (>100%). Recrystallization from tolueneisooctane gave 1.70 g of a white solid, m.p. 82°–84° C.

Analysis: Calculated for $C_{12}H_{29}NO_2$: C, 77.02; H, 8.93; N, 4.28. Found: C, 76.93; H, 9.03; N, 4.24.

EXAMPLE 29

2,3-Diphenylmorpholine.

β-[(2-Hydroxyethyl)amino]-α-phenylbenzeneethanol erythro isomer, 7.1 g (0.027 mole) was added to 20 ml of 70% sulfuric acid at 0° C. The mixture was heated at 100° C. for 3 hr and poured into ice and neutralized with 25% sodium hydroxide. The neutralized mixture was extracted with diethyl ether and the extract was dried and the solvent evaporated to give 5.8 g (54%), m.p. 70°–72° C. of solids. The solids were recrystallized from ethanol water mixture followed by low boiling petroleum ether, m.p. 82°–84° C.

Analysis: Calculated for $C_{16}H_{17}NO$: C, 80.36; H, 7.16. Found: C, 80.28; H, 7.35.

EXAMPLE 30

α-Phenyl-β-[(tetrahydrofuran-2-ylmethyl)amino]benzeneethanol

A mixture of trans-stilbene oxide (1.96 g, 0.010 mole) and tetrahydrofurfurylamine (3.03 g, 0.030 mole) was heated at 140° C. for 2 hrs. After standing at ambient temperature for 18 hrs, the mixture was diluted with water (150 ml). An oil separated from the solution which solidified on standing for an hour. NMR and mass spectral analyses showed stilbene oxide remaining. The solid was treated with another 3.03 g of tetrahydrofurfurylamine and the mixture heated at 140° C. for another 3 hours. The reaction mixture was treated with water (150 ml) as before to obtain 2.28 g (77%) of an off-white solid after drying under ambient conditions for 18 hours. The solid was recrystallized from toluene, m.p. 167°–168° C.

Analysis: Calculated for $C_{19}H_{23}NO_2$: C, 76.74; H, 7.80; N, 4.71. Found: C, 76.74; H, 8.05; N, 4.69.

EXAMPLE 31

β-[[3-(Hexyloxy)propyl]amino]-α-phenylbenzeneethanol.

A mixture of trans-stilbene oxide (1.96 g, 0.010 mole) and 3-hexyloxypropylamine (1.75 g, 0.011 mole) was heated at 140° C. for 6 hours. After standing at ambient temperature for 44 hours, the reaction mixture was dissolved in acetone (10 ml) and the solution poured into water (150 ml). The light brown oil which separated from solution solidified on standing for 1 hour. The solid was collected and dried on absorbent paper for 18 hours. The solid was then triturated in isooctane (soluble) and the solution chilled to obtain a solid which was collected, washed with cold isooctane, and dried under ambient conditions to obtain 1.20 g (34%) of the product, m.p. 67°–69° C.

Analysis: Calculated for $C_{23}H_{33}NO_2$: C, 77.70; H, 9.36; N, 3.93. Found: C, 77.75; H, 9.46; N, 3.99.

EXAMPLE 32

β-[(3-Hydroxypropyl)amino]-4-methyl-α-(4-methylphenyl)benzeneethanol, monohydrochloride, monohydrate.

A mixture of 4,4-dimethylbenzoin (4.31 g, 0.018 mole), 3-amino-1-propanol (4.04 g, 0.054 mole) aund phosphorus pentoxide (2.5 g) was heated for 4 hours in an oil bath at 105° C. with a nitrogen purge. After the reaction was complete, the contents were partitioned between chloform and water. The organic layer was washed with dilute acid (50×2 ml). The aqueous washes were combined, neutrallized and then washed with chloroform. The chloroform layer was concentrated then dissolved in ethanol (100 ml) to which solution an aqueous solution of sodium borohydride (2:1 mole ratio) was added. The reaction mixture was stirred for 1.5 hours then concentrated to dryness. The solid was partitioned between 25% sodium hydroxide (100 ml) and methylene chloride (100 ml). The organic layer was washed with water (2×100 ml), concentrated free base, 76.5% yield and dissolved in hot 2-propanol. A hydrochloric acid/isopropyl alcohol solution was added, solvent evaporated and methyl isobutyl ketone added to precipitate 1.25 g of crystals (24.9%), m.p. 179°–182° C.

Analysis: Calculated for $C_{19}H_{26}NO_2Cl$: C, 64.49; H, 7.98; N, 3.96. Found: C, 64.50; H, 7.46; N, 3.99.

EXAMPLE 33

β-[(2-Methoxyethyl)amino]-α-phenylbenzeneethanol, threo isomer, monohydrochloride.

A mixture of cis-stilbene oxide (1.96 g, 0.010 mole) and 2-methoxyethylamine (2.25 g, 0.030 mole) was heated on a steam bath for 18 hours. The reaction mixture was concentrated on a rotary evaporator to remove as much of the excess 2-methoxyethylamine as possible. The crude product was dissolved in ether and treated with excess ethereal hydrogen chloride solution. The solid was collected (1.77 g, 58% yield) and recrystallized from methanol-isopropyl ether. The product was dried under vacuum for 18 hours, m.p. 165°–166° C.

Analysis: Calculated for $C_{17}H_{22}NO_2Cl$: C, 66.33; H, 7.20; N, 4.55. Found: C, 66.40; H, 7.29; N, 4.57.

EXAMPLE 34

β-[(2-Hydroxycyclohexyl)amino]-α-phenylbenzeneethanol monohydrochloride.

A stirred suspension of 2-aminocyclohexanol, hydrochloride (3.03 g, 0.020 mole) in methanol (20 ml) was treated with 4.75 ml (0.20 mole) of 25% sodium methoxide in methanol. To this mixture was added trans-stilbene oxide (1.96 g, 0.010 mole), and the mixture concentrated on a rotary evaporator. The solid residue was heated at 125° C. for 16 hrs and then cooled to ambient temperature. The reaction mixture was dissolved in methanol (30 ml) and the solution poured into water (150 ml) causing the product to separate as a thick semisolid. The aqueous layer was decanted. The residual material was dissolved in methylene chloride, and the solution dried over anhydrous magnesium sulfate. The solution was concentrated to give 2.72 g (73%) of solid. The solid was dissolved in ether and treated with excess ethereal hydrogen chloride solution. The precipitate was collected to obtain 2.10 g of material which was recrystallized from absolute ethanol-isopropyl ether to give 1.55 g of crystals, m.p. 245°–248° C.

Analysis: Calculated for $C_{20}H_{26}NO_2Cl$: C, 69.05; H, 7.53; N, 4.03. Found: C, 68.94; H, 7.62; N, 4.04.

EXAMPLE 35

α-[[(Tetrahydrofuran-2-ylmethyl)amino]methyl]benzenemethanol

A mixture of styrene oxide (1.20 g, 0.010 mole) and tetrahydrofurfurylamine (4.05 g, 0.040 mole) was heated on a steam bath for 2 hours. After standing at ambient temperature for 60 hours the reaction mixture was dissolved in 10 ml of methanol and the solution poured into 120 ml of ice-water. The aqueous mixture was extracted with methylene chloride (50 ml). The extract was dried (over magnesium sulfate) and concentrated to give an oil which began to solidify within one hour. The material was triturated with petroleum ether to obtain 0.73 g of an off-white solid (33%). The solid was recrystallized from isooctane; m.p. 70°–72° C.

Analysis: Calculated for $C_{13}H_{14}NO_2$: C, 70.56; H, 8.65; N, 6.33. Found: C, 70.42; H, 8.70; N, 6.27.

EXAMPLE 36

2-[(2-Methoxyethyl)amino]-1-phenylpropanol

2-[(2-Methoxyethyl)amino]-1-phenyl-1-propanone hydrochloride as prepared in Preparation 5 is converted to the free base by mixing it with methylene chloride and a dilute basic aqueous solution, e.g., sodium hydroxide, separating the organic layer and evaporating the solvent. The residue, the free base is then reduced with sodium borohydride in ethanol to give the title compound which is then isolated by conventional means.

TABLE 1

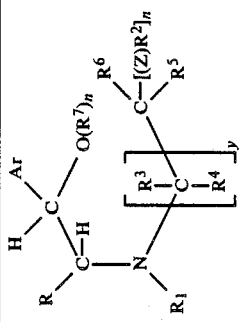

| Example No. | Ar | R | Z | R² | R¹ | $[R^3-C-R^4]_y$ | R⁵ | R⁶ | R⁷ | n | Salt | Isomer |
|---|---|---|---|---|---|---|---|---|---|---|---|---|
| 1 | 4-Cl—C₆H₄— | 4-Cl—C₆H₄— | O | H | H | —CH₂— | H | H | H | 1 | HCl | Erythro |
| 2 | C₆H₅— | C₆H₅— | O | H | H | —CH₂— | H | H | H | 1 | HCl | Erythro |
| 3 | 4-Cl—C₆H₄— | 4-Cl—C₆H₄— | S | H | H | —CH₂— | H | H | H | 1 | HCl | — |
| 4 | C₆H₅— | C₆H₅— | S | H | H | —CH₂— | H | H | H | 1 | HCl | — |
| 5 | C₆H₅— | C₆H₅— | O | H | H | —(CH₂)₂— | H | H | H | 1 | HCl | Erythro |
| 6 | C₆H₅— | C₆H₅— | O | C₂H₅ | H | —(CH₂)₂— | CH₃ | H | H | 1 | — | — |
| 7 | C₆H₅— | C₆H₅— | O | CH₃ | CH₃ | —CH₂— | H | H | H | 1 | — | — |
| 8 | C₆H₅— | C₆H₅— | O | H | H | —CH₂— | H | H | H | 1 | — | — |
| 9 | C₆H₅— | C₆H₅— | O | H | H | —CH₂— | H | H | H | 1 | HCl, 0.5H₂O | — |
| 10 | C₆H₅— | C₆H₅— | O | H | H | —(CH₂)₄— | H | H | H | 1 | HCl | Erythro |
| 11 | C₆H₅— | C₆H₅— | O | H | H | —(CH₂)₅— | H | H | H | 1 | HCl | Erythro |
| 12 | 4-OCH₃—C₆H₄— | 4-OCH₃—C₆H₄— | O | H | H | —(CH₂)₂— | H | H | H | 1 | Fumarate, 0.5H₂O | — |
| 13 | 4-OCH₃—C₆H₄— | 4-OCH₃—C₆H₄— | O | H | H | —(CH₂)₄— | H | H | H | 1 | HCl | — |
| 14 | 4-OCH₃—C₆H₄— | 4-OCH₃—C₆H₄— | O | H | H | —(CH₂)₅— | H | H | H | 1 | HCl | Erythro |
| 15 | C₆H₅ | C₆H₅ | O | H | H | —(CH₂)₃— | H | H | H | 1 | — | — |
| 16 | C₆H₅ | C₆H₅ | O | H | H | —CH—CH₃ | H | H | H | 1 | — | — |
| 17 | 4-OCH₃—C₆H₄— | H | O | —CH₃ | H | —CH₂— | H | H | H | 1 | — | — |
| 18 | 4-OCH₃—C₆H₄— | 4-OCH₃—C₆H₄— | O | H | H | —(CH₂)₃— | H | H | H | 1 | HCl, 0.5H₂O | — |
| 19 | 4-OCH₃—C₆H₄— | 4-OCH₃—C₆H₄— | O | H | H | —(CH₂)₂— | H | H | H | 1 | HCl, 0.5H₂O | — |
| 20 | C₆H₅ | C₆H₅ | O | H | H | —(CH₂)₂— | H | H | H | 1 | HCl | Threo |
| 21 | C₆H₅ | 4-(CH₃)₂N—C₆H₄ | O | H | H | —(CH₂)₂— | H | H | —CH₃ | 1 | — | — |
| 22 | C₆H₅ | C₆H₅ | O | —CH(CH₃)₂ | H | —CH₂— | H | H | H | 1 | — | — |
| 23 | C₆H₅ | H | O | —CH₂CH(CH₃)₂ | H | —(CH₂)₂— | H | H | H | 1 | HCl, 0.5H₂O | — |
| 24 | 4-Cl—C₆H₄— | 4-Cl—C₆H₄ | O | H | H | —(CH₂)₂— | H | H | H | 1 | — | — |
| 25 | C₆H₅ | C₆H₅ | O | —(CH₂)₃CH₃ | H | —(CH₂)₂— | H | H | H | 1 | HCl | — |
| 26 | C₆H₅ | C₆H₅ | O | H | H | —(CH₂)₂— | H | H | H | 1 | HCl, 0.5H₂O | — |
| 27 | 4-CH₃—C₆H₄— | 4-CH₃—C₆H₄ | O | H | H | —(CH₂)₂— | H | H | H | 1 | HCl | — |
| 28 | C₆H₅ | C₆H₅ | O | H | H | —CH₂— | H | H | H | 1 | — | — |
| 29 | C₆H₅ | C₆H₅ | (a) | (b) | H | —CH₂— | (b) | (b) | (a) | 0 | — | — |
| 30 | C₆H₅ | C₆H₅ | O | H | H | —CH₂— | H | H | H | 1 | — | — |

TABLE 1-continued $$R-\overset{H}{\underset{\overset{|}{C}-N}{C}}\overset{Ar}{\underset{R_1}{\underset{|}{-}}}\quad \overset{O(R^7)_n}{\underset{[\overset{R^3}{\underset{R^4}{\underset{|}{C}}}]_y}{-}}\overset{R^6}{\underset{R^5}{\underset{|}{C}-[(Z)R^2]_n}}$$

| Example No. | Ar | R | Z | R² | R¹ | $\begin{bmatrix} R^3 \\ -C- \\ R^4 \end{bmatrix}_y$ | R⁵ | R⁶ | R⁷ | n | Salt | Isomer |
|---|---|---|---|---|---|---|---|---|---|---|---|---|
| 31 | C₆H₅ | C₆H₅ | O | —(CH₂)₅CH₃ | H | —(CH₂)₂— | H | H | H | 1 | — | — |
| 32 | 4-CH₃—C₆H₄— | 4-CH₃—C₆H₄— | O | H | H | —(CH₂)₂— | H | H | H | 1 | HCl.H₂O | threo |
| 33 | C₆H₅ | C₆H₅ | O | —CH₃ | H | —CH₂— | (c) | H | H | 1 | — | — |
| 34 | C₆H₅ | C₆H₅ | O | H | H | (c) | (b) | (b) | H | 1 | HCl | — |
| 35 | C₆H₅ | H | O | (b) | H | —CH₂— | H | H | H | 1 | — | — |
| 36 | C₆H₅ | —CH₃ | O | —CH₃ | H | —CH₂— | H | H | H | 1 | — | — |

(a) R⁷ and ZR² do not exist and a morpholine ring is formed.
(b) R⁵ and (ZR²)n taken together form tetrahydrofuran 2-yl.
(c) $-\overset{R^3}{\underset{R^4}{\underset{|}{C}-}}$ and CR⁵R⁶ form one side of a cyclohexyl group.

VIROLOGICAL TESTING

(1) Antiviral Test Procedure, Experimental Compounds vs Bovine Parainfluenza-3(Shipping Fever-4) Virus in Cell Culture The test system consists of monolayers of a continuous bovine kidney cell line, the MDBK-cell, infected with a standard dose of bovine parainfluenza-3 virus, and incubated for 72 hours at 35° C.

Experimental compounds are made up in tissue culture medium and applied to the cell monolayers according to the following scheme:

one set of cells is treated with compounds at 10 mcg-1 mg concentrations immediately after the cells have been infected-control infected cells with tissue culture medium alone;

a second set of normal cells is treated with the same concentrations of compound-the normal control cells receive tissue culture fluid alone.

The first set of cells comprises the antiviral test itself, and the second set of uninfected cells serves as a toxicity control system.

At the end of the 72-hour incubation period, monolayers are inoculated and incubated for 2 hours with the vital stain and then measured spectrophotometrically.

Toxicity Readings

Compounds are read first for toxicity; uninfected cells treated with concentrations of compound that allow at least 75% of the vital stain retention seen in untreated, uninfected cells are considered non-toxic.

Antiviral Readings

Treated, infected cells that retain at least 50% more vital stain than the infected control cells are read as being protected by antiviral effects of the compound.

EXAMPLES OF POSITIVE ANTIVIRAL RESULTS

| Toxicity Results | |
|---|---|
| Untreated, Uninfected Cells | 100% Dye Retention |
| 10 mcg. cpd. Example 1 | 100% Dye Retention non-toxic levels |
| 50 mcg. cpd. Example 1 | 90% Dye Retention non-toxic levels |
| 100 mcg. cpd. Example 1 | 80% Dye Retention non-toxic levels |
| 200 mcg. cpd. Example 1 | 75% Dye Retention non-toxic levels |
| 500 mcg. cpd. Example 1 | 50% Dye Retention |
| Antiviral Results | |
| Untreated, infected cells | 10% Dye Retention |
| 10 mcg. cpd. Example 1 | 20% Dye Retention |
| 50 mcg. cpd. Example 1 | 60% Dye Retention active antiviral levels |
| 100 mcg. cpd. | 70% Dye Retention active antiviral levels |
| 200 mcg. cpd. | 70% Dye Retention active antiviral levels |

(2) Antiviral Test Procedure, Antiviral Activity of Experimental Compounds in Germfree Animals Infected with Bovine Parainfluenza-3 (PI 3) Virus Test animals (calves) were delivered at birth by hysterectomy and placed on individual isolators. The animals were never removed from isolation and all experimental work was done within the isolation unit and was maintained SPF (specific pathogen free) throughout the test.

The pool of virus used in testing was derived by infecting primary bovine kidney cells with Bovine Parainfluenza-3 Virus and allowing cytopathogenic effects in cell culture (CPE) to develop. The cells were frozen and thawed and the virus was filtered with a 0.22μ filter, placed in 2 ml portions and stored at $-70°$ C. This virus was HA positive, heat sensitive and ether sensitive.

On day 0, the animals were injected subcutaneously with a sterile water solution of the drug or sterile carrier (water) depending upon the animal's role as test drug subject or as control. Two hours later, all calves were infected intranasally via aerosol with $1 \times 10^6 TCID_{50}$ (tissue culture infective doses). Animals were reinjected with drug or carrier 6 hr. later, and twice daily for four more days.

Table 2 summarizes the effect of administration of 75 mg/kg of the compound of Example 1 in the calf lung and indicates a marked (82%) reduction in the disease process of viral pneumonia and bronchitis occurred after 5 days as compared to controls.

TABLE 2

Index of Bronchiolitis and Pneumonia
5 Days After Parainfluenza-3 Viral Infection

| Parameter | Vehicle Control (3 Calves) | Treated with Compound of Example 1 (4 Calves) |
|---|---|---|
| Bronchiolitis (% airways affected)* | 77.29 ± 13.59[a] | 56.70 ± 11.69[b] |
| Pneumonia | 11.24 ± 6.86 | 2.06 ± 0.81[c] |

[a]Mean ± s.d.
[b]p = 0.08, two-tailed t-test.
[c]p = 0.04.
*tissue necropsy observation.

FORMULATION AND ADMINISTRATION

The compounds of Formula I are administered subcutaneously to animals such as have been or will be infected by shipping fever virus. Various carriers known in the art are possible; however, an aqueous medium is preferred. The compounds in a suitable carrier such as are commonly used for subcutaneous implants may also be in the form of a bolus or pellets so as to further provide for gradual release. Dosages vary from about 10 to 100 mg/kg, preferably about 10 to 75 mg/kg, and appear to be suitably administered during a period of time which would cover the stress period of shipping the animal and a reasonable adjustment period. The exact individual doses will, of course, be determined under the direction of a veterinarian.

What is claimed is:

1. A method of combating viral infections due to bovine parainfluenza-3 virus (shipping fever virus) in animals which comprises administering to said animals a compound selected from the group having the formula in an amount effective to control shipping fever virus:

$$\begin{array}{c} R \\ \diagdown \\ CH \\ R^1-N \end{array} \begin{array}{c} H \\ \diagdown \\ C \\ \diagup \\ \left[\begin{array}{c} R^3 \\ | \\ C \\ | \\ R^4 \end{array}\right]_y \end{array} \begin{array}{c} Ar \\ \diagup \\ O-(R^7)_n \\ \diagdown \\ R^6 \\ C-(ZR^2)_n \\ \diagdown \\ R^5 \end{array}$$

wherein;

Ar is

Z is oxygen or sulfur;
R is selected from hydrogen, loweralkyl, or

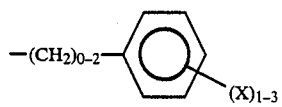

$R^1$, $R^2$, $R^3$, $R^4$, $R^5$, $R^6$ and $R^7$ are selected from hydrogen or loweralkyl;

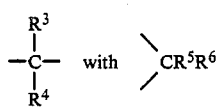

together may form a lowercycloalkyl group (3–9 carbons); or $R^5$ with $ZR^2$ when taken together may form a 5-membered saturated oxygen or sulfur containing heterocyclic ring;
X is selected from hydrogen, halo, loweralkoxy, loweralkyl, trifluoromethyl or dimethylamino, and when X is more than 1, it may be the same radical or different;
y is 0, 1 or 2;
n is 1 or zero and when n is 1, the stereoisomers thereof, and when n is zero the dotted line becomes an oxygen-carbon bond forming a ring, and the pharmaceutically acceptable acid addition salts of all thereof.

2. The method of claim 1 wherein the compound administered is 4-chloro-α-(4-chlorophenyl)-β-[2-(hydroxyethyl)amino]benzeneethanol, a stereoisomer, or a pharmaceutically acceptable acid addition salt thereof.

3. The method of claim 1 wherein the compound administered is β-[(2-hydroxyethyl)amino]-α-phenylbenzeneethanol, a stereoisomer, or a pharmaceutically acceptable acid addition salt thereof.

4. The method of claim 1 wherein the compound administered is 4-chloro-α-(b 4-chlorophenyl)-β-[(2-mercaptoethyl)amino]benzeneethanol, a stereoisomer, or a pharmaceutically acceptable salt thereof.

5. The method of claim 1 wherein the compound administered is β-[(2-mercaptoethyl)amino]-α-phenylbenzeneethanol, a stereoisomer, or a pharmaceutically acceptable acid addition salt thereof.

6. The method of claim 1 wherein the compound administered is α-[(3-hydroxypropyl)amino]phenylmethyl]benzenemethanol, a stereoisomer, or a pharmaceutically acceptable acid addition salt thereof.

7. The method of claim 1 wherein the compound administered is β-[(2-hydroxypropyl)amino]-α-phenylbenzeneethanol, a stereoisomer, or a pharmaceutically acceptable acid addition salt thereof.

8. The method of claim 1 wherein the compound administered is β-[(2-ethoxyethyl)amino]-α-phenylbenzeneethanol, a stereoisomer, or a pharmaceutically acceptable acid addition salt thereof.

9. The method of claim 1 wherein the compound administered is β-[(2-methoxyethyl)amino]-α-phenylbenzeneethanol, a stereoisomer, or a pharamceutically acceptable acid addition salt thereof.

10. The method of claim 1 wherein the compound administered is β-[(2-hydroxyethyl)methylamino]-α-phenylbenzeneethanol, a stereoisomer, or a pharmaceutically acceptable acid addition salt thereof.

11. The method of claim 1 wherein the compound administered is α-[[(5-hydroxypentyl)amino]phenylmethyl]benzenemethanol, a stereoisomer, or a pharmaceutically acceptable acid addition salt thereof.

12. The method of claim 1 wherein the compound administered is α-[[(6-hydroxyhexyl)amino]phenylmethyl]benzenemethanol, a stereoisomer, or a pharmaceutically acceptable acid addition salt thereof.

13. The method of claim 1 wherein the compound administered is β-[(3-hydroxypropyl)amino]-4-methoxy-α-(4-methoxyphenyl)benzeneethanol, a stereoisomer, or a pharmaceutically acceptable acid addition salt thereof.

14. The method of claim 1 wherein the compound administered is β-[(5-hydroxypentyl)amino]-4-methoxy-α-(4-methoxyphenyl)benzeneethanol, a stereoisomer, or a pharmaceutically acceptable acid addition salt thereof.

15. The method of claim 1 wherein the compound administered is β-[(6-hydroxyhexyl)amino]-4-methoxy-α-(4-methoxyphenyl)benzene ethanol, a stereoisomer, or a pharmaceutically acceptable acid addition salt thereof.

16. The method of claim 1 wherein the compound administered is β-[(4-hydroxybutyl)amino]-α-phenylbenzeneethanol, a stereoisomer, or a pharmaceutically acceptable acid addition salt thereof.

17. The method of claim 1 wherein the compound administered is β-[(2-hydroxy-1-methylethyl)amino]-α-phenylbenzeneethanol, a stereoisomer, or a pharmaceutically acceptable acid addition salt thereof.

18. The method of claim 1 wherein the compound administered is α-[[(2-methoxyethyl)amino]methyl]benzenemethanol, a stereoisomer, or a pharmaceutically acceptable acid addition salt thereof.

19. The method of claim 1 wherein the compound administered is β-[(4-hydroxybutyl)amino]-4-methoxy-α-(4-methoxyphenyl)benzeneethanol, a stereoisomer, or a pharmaceutically acceptable acid addition salt thereof.

20. The method of claim 1 wherein the compound administered is β-[(2-hydroxyethyl)amino]-4-methoxy-α-(4-methoxyphenyl)benzeneethanol, a stereoisomer, or a pharmaceutically acceptable acid addition salt thereof.

21. The method of claim 1 wherein the compound administered is 4-(dimethylamino)-β-[(2-hydroxyethyl)amino]-α-phenylbenzeneethanol, a stereoisomer, or a pharmaceutically acceptable acid addition salt thereof.

22. The method of claim 1 wherein the compound administered is 2-[(2-methoxy-1,2-diphenylethyl)amino]ethanol, a stereoisomer, or a pharmaceutically acceptable acid addition salt thereof.

23. The method of claim 1 wherein the compound administered is α-[[(2-hydroxyethyl)amino]methyl]benzenemethanol, a stereoisomer, or a pharmaceutically acceptable acid addition salt thereof.

24. The method of claim 1 wherein the compound administered is 4-chloro-α-(4-chlorophenyl)-β-[(2-hydroxyethyl)amino]benzeneethanol, a stereoisomer, or a pharmaceutically acceptable acid addition salt thereof.

25. The method of claim 1 wherein the compound administered is β-[[3-(1-methylethoxy)propyl]amino]-α-phenylbenzeneethanol, a stereoisomer, or a pharmaceutically acceptable acid addition salt thereof.

26. The method of claim 1 wherein the compound administered is β-[[3-(2-methylpropoxy)propyl]amino]-α-phenylbenzeneethanol, a stereoisomer, or a pharmaceutically acceptable acid addition salt thereof.

27. The method of claim 1 wherein the compound administered is β-[(2-hydroxyethyl)amino]-4-methyl-α-(4-methylphenyl)benzeneethanol, a stereoisomer, or a pharmaceutically acceptable acid addition salt thereof.

28. The method of claim 1 wherein the compound administered is β-[(3-butoxypropyl)amino]-α-phenylbenzeneethanol, a stereoisomer, or a pharmaceutically acceptable acid addition salt thereof.

29. The method of claim 1 wherein the compound administered is 2,3-diphenylmorpholine or a pharmaceutically acceptable acid addition salt thereof.

30. The method of claim 1 wherein the compound administered is α-phenyl-β-[(tetrahydrofuran-2-ylmethyl)amino]benzeneethanol, a stereoisomer, or a pharmaceutically acceptable acid addition salt thereof.

31. The method of claim 1 wherein the compound administered is β-[[3-(hexyloxy)propyl]amino]-α-phenylbenzeneethanol, a stereoisomer, or a pharmaceutically acceptable acid addition salt thereof.

32. The method of claim 1 wherein the compound administered is β-[(3-hydroxypropyl)amino]-4-methyl-α-(4-methylphenyl)benzeneethanol, a stereoisomer, or a pharmaceutically acceptable acid addition salt thereof.

33. The method of claim 1 wherein the compound administered is β-[(2-methoxyethyl)amino]-α-phenylbenzeneethanol, a stereoisomer, or a pharmaceutically acceptable acid addition salt thereof.

34. The method of claim 1 wherein the compound administered is β-[(2-hydroxycyclohexyl)amino]-α-phenylbenzeneethanol, a stereoisomer, or a pharmaceutically acceptable acid addition salt thereof.

35. The method of claim 1 wherein the compound administered is α-[[(tetrahydrofuran-2-ylmethyl)amino]methyl]benzenemethanol, a stereoisomer, or a pharmaceutically acceptable acid addition salt thereof.

36. The method of claim 1 wherein the compound administered is 2-[(2-methoxyethyl)amino]-1-phenylpropanol, a stereoisomer, or a pharmaceutically acceptable acid addition salt thereof.

* * * * *